United States Patent [19]

Sebastian

[11] Patent Number: 5,196,575
[45] Date of Patent: Mar. 23, 1993

[54] SUPERCRITICAL SEPARATION OF ISOMERS OF FUNCTIONAL ORGANIC COMPOUNDS AT MODERATE CONDITIONS

[75] Inventor: Mark J. Sebastian, Lebanon, N.J.

[73] Assignee: Hoechst Celanese Corp., Somerville, N.J.

[21] Appl. No.: 838,387

[22] Filed: Feb. 19, 1992

[51] Int. Cl.$^5$ .............................................. C07B 57/00
[52] U.S. Cl. .................................. 562/402; 562/467; 568/742
[58] Field of Search ................. 562/402, 467; 568/742

[56] References Cited

U.S. PATENT DOCUMENTS

| | | | |
|---|---|---|---|
| 4,417,070 | 11/1983 | Arai et al. | 562/402 |
| 4,514,574 | 4/1985 | Inoue et al. | 502/424 |
| 4,550,198 | 10/1985 | Myerson | 560/486 |
| 4,622,419 | 11/1986 | Cannala et al. | 562/402 |
| 4,652,675 | 3/1987 | Goorden et al. | 562/494 |
| 4,654,437 | 3/1987 | Goorden et al. | 562/494 |
| 4,724,102 | 2/1988 | Cannala et al. | 562/402 |
| 4,783,548 | 11/1988 | Zoeller | 562/467 |
| 4,795,596 | 1/1989 | Hammerschmidt | 506/467 |
| 4,865,770 | 9/1989 | Piselli | 562/402 |
| 4,983,765 | 1/1991 | Lukas | 562/402 |

OTHER PUBLICATIONS

R. T. Marentis, "Steps to Developing a Commercial Supercritical Carbon Dioxide Processing Plant", ACS Symposium Series, #366, 127-143, (1988).

Krukonis et al., "Solubility of Solid Aromatic Isomers in Carbon Dioxide", J. Chem. Eng. Data, 1985, 30, 247-249.

T. A. Berger and J. F. Deye "Separation of Hydroxybenzoic Acids by Packed Column Supercritical Fluid Chromatography Using Modified Fluids with Very Polar Additives", J. Chromatogr. Sci, 29, 26-30 (1991).

T. A. Berger and J. F. Deye "Separation of Benzene Polycarboxylic Acids by Packed Column Supercritical Fluid Chromatography Using Methanol-Carbon Dioxide Mixtures with Very Polar Additives", J. Chromatogr. Sci 29, 141-146, (1991).

*Primary Examiner*—Paul J. Killos
*Attorney, Agent, or Firm*—Michael W. Ferrell

[57] ABSTRACT

A method of separating isomers of functionalized aromatic compounds using solvent-modified supercritical carbon dioxide is disclosed and claimed. In one embodiment, isomers of hydroxynaphthoic acid are separated by selective extraction of the more soluble species.

16 Claims, 1 Drawing Sheet

SUPERCRITICAL SEPARATION OF ISOMERS OF FUNCTIONAL ORGANIC COMPOUNDS AT MODERATE CONDITIONS

TECHNICAL FIELD

The present invention relates generally to supercritical separation of organic compounds utilizing solubility differences, and more particularly, to supercritical separation using solvent-modified carbon dioxide as a processing medium to purify isomers of functional aromatic organic molecules for use as monomers for polymer synthesis.

BACKGROUND OF INVENTION

The applications of supercritical fluids as solvents for extracting or separating chemicals, foods and beverage products is increasing as seen in both the technical and patent literature. See, e.g., Pat Tap-10 Patent Technology Review: Supercritical Fluids—"Applications and Materials", Business Communications Co. Inc. 25 Van-Zant St. Norwalk, Conn. 06855. Applications such as the decaffeination of coffee, extraction of herbs, spices, and separating alcohol and water have been described. Among the many advantages of supercritical separation are that the extract is essentially solvent-free when the solution is de-pressurized and the fluid can be re-cycled. Thus, supercritical systems may be operated without substantial waste streams of contaminated solvent.

Despite interest in generally applying supercritical technology within the chemical industry, such processes have usually been applied to extracting non-polar components from naturally occurring substances such as petroleum, seed oils, or the like. It has been found useful to use a co-solvent such as methanol or water to increase the solubility of compounds in supercritical carbon dioxide. See R. T. Marentis, "Steps to Developing a Commercial Supercritical Carbon Dioxide Processing Plant" ACS Symposium Series, #366 127–143, (1988).

In practical terms, a major obstacle to the commercialization of carbon dioxide-based supercritical processes for selected systems, especially functional aromatic systems which contain compounds suitable for use as monomer reactants, is that functional aromatic compounds of interest tend to have relatively low solubility at moderate pressures.

Although extractions may occur at higher pressures, the increased cost of capital for high pressure hardware and higher energy costs incurred in achieving the high pressures and recycling the gas to these pressures, has made high pressure extraction prohibitively expensive.

Krukonis et al, J. Chem.. Eng. Data, 1985, 30, 247–249, report a difference of roughly two orders of magnitude in the solubility of isomers of hydroxybenzoic acid in carbon dioxide at approximately 200+ atmospheres and 100° C.; the ortho and meta hydroxybenzoic acids being much more soluble than the para isomer. Others have reported rapid separations of isomers of hydroxy-benzoic acid using supercritical carbon dioxide chromatography with modified fluids. See Berger and Deye "Separation of Hydroxybenzoic Acids by Packed Column Supercritical Fluid Chromatography using Modified Fluids with Very Polar Additives", J. Chromatogr. Sci, 29, 26–30 (1991) and "Separation of Benzene Polycarboxylic Acids by Packed Column Supercritical Fluid Chromatography Using Methanol-Carbon Dioxide Mixtures with Very Polar Additives", J. Chromatogr. Sci 29, 141–146 (1991). The foregoing articles report the use of carbon dioxide/methanol mixtures as the supercritical fluid in chromatographic systems with highly polar additives such as trifluoroacetic acid present.

DESCRIPTION OF INVENTION

It has been found that the use of small amounts of polar modifiers sufficiently increase the solubility properties of supercritical fluid carbon dioxide that polar compounds such as isomers of hydroxy-acids can be separated with the fluid pressure relatively close to the critical point. In this manner, a lower process pressure is obtained and less energy is required for recompression of the expanded gas.

In general, the invention involves:
 (a) delivering a flowing supercritical fluid, the major component of which is carbon dioxide and a minor proportion of which is a polar solvent to form solvent-modified carbon dioxide;
 (b) contacting a mixture containing at least first and second isomers of a functionalized aromatic organic compound with the flowing solvent-modified supercritical carbon dioxide in a suitable apparatus at a temperature of at least about 30° Celsius and a pressure of at least about 70 atmospheres to selectively extract said first isomer such that the residue becomes enriched with said second isomer; and
 (c) precipitating said first isomer from said flowing solvent-modified carbon dioxide by expanding the gas stream to a pressure substantially below 70 atmospheres.

The mixture containing the isomers may be in a solid state and the polar solvent is typically selected from the group consisting of water, methanol, isopropanol, tetrahydrofuran, dimethylacetamide, acetone, organic acids or mixtures thereof.

Moreover, halogenated solvents such as dichloromethane, and the fluorocarbons exhibit unique solvent selectivity.

In one embodiment, the solvent modified carbon dioxide supercritical fluid consists of carbon dioxide and methanol.

Generally, the polar solvent is present in an amount of from about 0.1 to about 15 weight percent of the solvent-modified carbon dioxide.

Generally speaking, the process is carried out at a pressure between about 80 and 150 atmospheres; with a pressure of between about 95 and 125 atmospheres being more typical. Particularly preferred are from about 100 to about 115 atmospheres.

Although any temperature above the pseudo critical temperature of the mixture may be used, the inventive process generally is carried out at a temperature of from about 30 to about 200 degrees Celsius; 30 to 100 degrees Celsius being more typical. At higher temperatures unwanted side reactions might occur with polar compounds such as alcohols and esters.

The isomer-containing mixture may contain suitable isomers of aromatic hydroxy-acids, hydroquinones, aromatic diamines, aromatic diacids, aromatic diesters, mixed aromatic acid-esters, or halogenated aromatic compounds. The system should be selected with care, for example, the isomer pair 3,3' diaminodiphenylsulfone, 4,4' diaminodiphenylsulfone may be substantially inert with respect to carbon dioxide under conditions of interest; while pairs of isomers of other aromatic diamines may be reactive enough to form urethanes or the like. Such reactions are to be avoided in general. Typical isomers of functional aromatic compounds which may be separated in accordance with the present invention include those with fused diaryl nucleii, for example isomers of hydroxynaphthoic acid. In a specific embodiment described hereinafter, 2-hydroxynaphthalene and 3-hydroxy-2-naphthoic acid are extracted from a mixture with 6-hydroxy-2-naphthoic acid ("6,2 acid") such that the residue consists of the 6,2 acid isomer.

BRIEF DESCRIPTION OF DRAWINGS

The invention is described in detail below in connection with a single FIGURE which is a schematic diagram of an apparatus useful in connection with the present invention.

DETAILED DESCRIPTION

Figure 1:
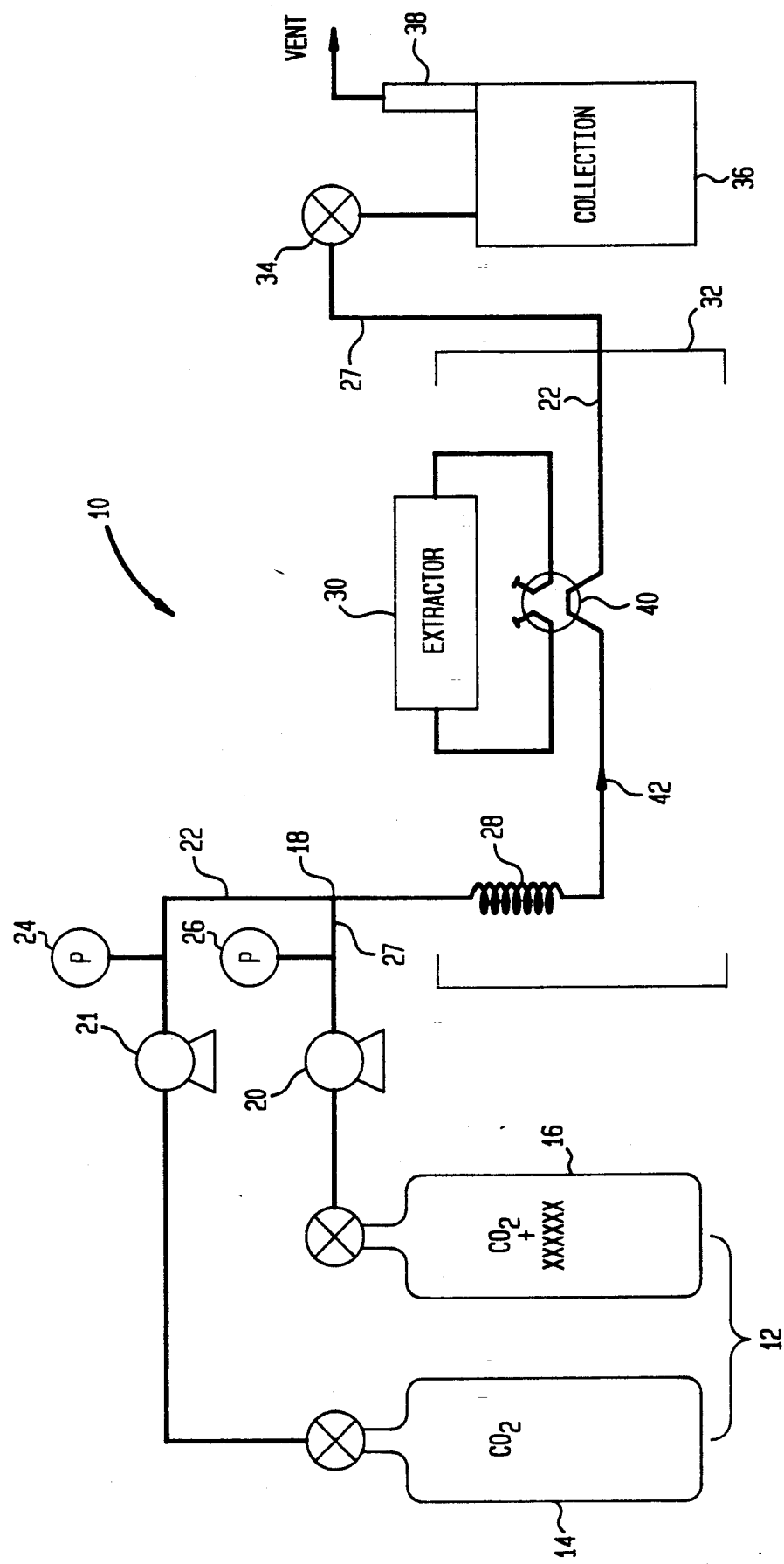

The invention is exemplified hereinafter for purposes of illustration and not by way of limitation. For example, it would be readily apparent to one of skill in the art to use ethanol as a solvent modifier instead of methanol as is the case with an illustration which follows.

The invention in one embodiment may be practiced in connection with an apparatus 10 shown schematically in FIG. 1. The apparatus includes a fluid source 12, which may be bottled gas as shown. Bottle 14 contains neat carbon dioxide while bottle 16 contains carbon dioxide with ten weight percent methanol. Adjustment of the mixture to the desired composition is achieved by adjustment of the volumetric flow rates of the two pumps 20, 21.

Pumps 20, 21 are connected via suitable flow conduit 22 to a mixing tee 18. Preferably, a pair of pressure regulators 24, 26 are provided. Downstream of mixing tee 18, a heating coil 28 is provided to bring the supercritical fluid to the extraction temperature; preferably an extraction vessel 30 is also located within an oven indicated generally at 32. Vessel 30 may be a standard HPLC guard column. Downstream of vessel 30 there is provided a high speed back pressure valve 34 to maintain the system pressure. Alternatively, one could use a fixed valve and regulate pressure by way of the volumetric flow rate through the system. After passing valve 34, flowing fluid enters collection vessel 36 which is vented at 38 such that it is at essentially at atmospheric pressure. If so desired, in lieu of a vent, a recirculation system could be added so that fluid may be recirculated. Likewise if recirculation was desirable under certain conditons, it could be accomplished at other points in the system, for example, to improve mixing or solvation.

Extractor vessel 30 may be connected with a multiport valve 40 so that it can be switched off and on the flow circuit of conduit 22. Optionally, a chromatographic column (not shown) can be added downstream of vessel 30 if so desired. Such a system provides a loading of solids directly to the chromatographic column.

EXAMPLE I

An 8:1:1 mixture of 6-hydroxy-2-naphthoic acid ("6,2 HNA"), 3-hydroxy-2-naphthoic acid ("3,2 HNA"), and 2-naphthanol ("2-NOH") was prepared as follows:

4 grams of approximately 98% pure 6,2 HNA, 0.5 grams of 3,2 HNA (Aldrich Chemical) and 0.5 grams of 2-NOH were mixed in a sample vial, and tumbled for fifteen (15) minutes in a Spex 8000 shaker.

Roughly 100 mg of the powdered mixture so prepared was placed in extraction vessel 30 of FIG. 1.

Apparatus 10 was then brought to a temperature of fifty (50) degrees Celsius at region 32 and a flow of 3 milliliters per minute through the system in the direction indicated by arrow 42 was initiated with 3.3 weight percent methanol, the balance being $CO_2$. The foregoing was achieved by adjusting the volumetric flow of pumps 20 and 21. The pressure of the system upstream of valve 34 was maintained at 110 $kg/cm^2$ or about 100 atm. Once the system was equilibrated at the foregoing conditions, the sample was switched in line by the multiport valve 40 and the system was operated for 30 minutes at 50 degrees Celsius and 110 $kg/cm^2$ atmospheres pressure, the extract being collected in vessel 38. After this extract (extract #1) was removed, a fresh vessel 36 was replaced, and the system was operated for an additional thirty (30) minutes, providing extract #2. High performance liquid chromatography was performed on the initial mixture, the two extracts and the residue. The residue after 60 minutes was substantially all 6, 2 HNA, that is, free of 3,2 HNA and 2-NOH, the same being true of extract #2. Extract #1 thus contained substantially all of the 2-NOH and 3,2 HNA, suggesting a fluid solubility in excess of about 0.20 milligrams of 2-NOH and 3,2 HNA per milliliter of supercritical fluid over the initial extraction period.

EXAMPLE II

Example I was substantially repeated, except that only 6,2 HNA was placed in the extraction vessel and no methanol as used in the supercritical fluid. No weight loss of the 6,2 HNA sample occurred after 30 minutes of operation.

EXAMPLE III

Example I was substantially repeated except that only 3,2 HNA was placed in the extraction vessel, and neat carbon dioxide was used as the supercritical fluid. Only approximately one percent (1%) weight loss occurred after 30 minutes which could have been due to impurities in the sample.

EXAMPLE IV

Example I was substantially repeated except that only 2-NOH was placed in the extraction vessel and neat carbon dioxide was used as in examples II and III. After 30 minutes about eleven percent (11%) of the material was extracted by the supercritical fluid.

Although the invention has been described in detail hereinabove, various modifications will be apparent to those of skill in the art; for example the amount of solvent modifier could be varied depending upon the operating conditions desired. Such modifications are within the spirit and scope of the present invention which is further described in the appended claims.

I claim:

1. A method of separating isomers of functionalized aromatic compounds using a supercritical gas mixture consisting essentially of:
    (a) preparing a supercritical fluid, the major component of which is carbon dioxide and a minor proportion of which is a polar solvent to form solvent-modified carbon dioxide and imparting flow to said solvent-modified supercritical carbon dioxide;

(b) contacting a mixture containing at least first and second isomers of a functionalized aromatic organic compound with said flowing solvent-modified supercritical carbon dioxide in a suitable apparatus, said mixture being substantially inert with respect to said solvent-modified supercritical carbon dioxide, at a temperature of at least about 30° Celsius and a pressure of at least about 70 atmospheres to, selectively extract said first isomer from said mixture essentially by way of interaction with said solvent-modified supercritical carbon dioxide such that the mixture residue becomes enriched with said second, isomer; and (c) precipitating said first isomer from said flowing solvent-modified carbon dioxide by expanding the gas stream to a pressure substantially below 70 atmospheres.

2. The method according to claim 1, wherein the mixture is in a solid state.

3. The method according to claim 1, wherein the polar solvent is selected from the group consisting of water, organic alcohols, methanol, isopropanol, tetrahydrofuran, dimethylacetamide, acetone, an organic acid or mixtures thereof.

4. The method according to claim 3, wherein said supercritical fluid consists essentially of carbon dioxide and methanol.

5. The method according to claim 1, wherein said polar solvent is present in an amount of from about 0.1 to about 15 weight per cent of the solvent-modified carbon dioxide.

6. The method according to claim 1, wherein said step of contacting said mixture with said solvent-modified supercritical carbon dioxide is carried out at a pressure between about 80 and 150 atmospheres, being abot the pseudo-critical pressure of the mixture.

7. The method according to claim 6, wherein said pressure is between about 95 and 125 atmospheres.

8. The method according to claim 7, wherein said pressure is from about 100 to about 115 atmospheres.

9. The method according to claim 1, wherein said step of contacting said mixture with said solvent-modified supercritical carbon dioxide is carried out at a temperature of from about 30° to about 200° degrees Celsius.

10. The method according to claim 9, wherein said temperature is from about 30° to about 100° degrees Celsius.

11. The method according to claim 1, wherein said mixture contains at least a pair of geometric isomers of functional aromatic compounds selected from the group consisting of aromatic hydroxy-acids, aromatic diamines, aromatic diesters, mixed aromatic acid esters, aromatic diacids and halogenated aromatic compounds.

12. The method according to claim 11 wherein said pair of geometric isomers are of a compound with a diaryl nucleus of the naphthalene or biphenyl type.

13. The method according to claim 12, wherein said pair of isomers are isomers of hydroxy-naphthoic acid.

14. The method according to claim 13, wherein at least one of said isomers is 6-hydroxy-2-naphthoic acid.

15. A method of separating a mixture including at least 2-hydroxynaphthalene, 6-hydroxy-2-naphthoic acid and 3-hydroxy-2-naphthoic acid comprising:

(a) preparing a supercritical fluid, the major component of which is carbon dioxide and a minor proportion of which is a polar solvent to form solvent-modified carbon dioxide and imparting flow to said solvent-modified supercritical carbon dioxide; and (b) preparing a mixture containing 2-hydroxynaphthalene, 6-hydroxy-2-naphthoic acid and 3-hydroxy-2-naphthoic acid; and (c) contacting said mixture with said flowing solvent modified supercritical carbon dioxide in a suitable apparatus at a temperature of at least about 30° Celsius and a pressure of at least about 70 atmospheres to selectively extract 2-hydroxynaphthalene and 3-hydroxy-2-naphthoic acid from said mixture whereby the residue becomes enriched with 6-hydroxy-2-naphthoic acid.

16. The method according to claim 15, wherein the residue consists essentially of 6-hydroxy-2-naphthoic acid.

* * * * *